(12) United States Patent
Choux et al.

(10) Patent No.: US 9,216,038 B2
(45) Date of Patent: Dec. 22, 2015

(54) DEVICE FOR OSTEOSYNTHESIS OF THE THORACIC WALL

(75) Inventors: Christian Choux, Savigneux (FR); Olivier Tiffet, Saint-Just-Saint-Rambert (FR)

(73) Assignee: UNIVERSITÉ JEAN MONNET, Saint Etienne (FR)

( * ) Notice: Subject to any disclaimer, the term of this patent is extended or adjusted under 35 U.S.C. 154(b) by 181 days.

(21) Appl. No.: 13/521,322

(22) PCT Filed: Jan. 21, 2011

(86) PCT No.: PCT/FR2011/050121
§ 371 (c)(1),
(2), (4) Date: Jul. 10, 2012

(87) PCT Pub. No.: WO2011/092417
PCT Pub. Date: Aug. 4, 2011

(65) Prior Publication Data
US 2012/0296440 A1    Nov. 22, 2012

(30) Foreign Application Priority Data
Jan. 26, 2010    (FR) .................................... 10 00275

(51) Int. Cl.
*A61B 17/68*    (2006.01)
*A61B 17/80*    (2006.01)

(52) U.S. Cl.
CPC ............. *A61B 17/68* (2013.01); *A61B 17/8076* (2013.01)

(58) Field of Classification Search
CPC .... A61F 2/95; A61B 17/8076; A61B 17/823; A61B 17/7062; A61B 17/3447; A61B 17/68
USPC .................. 623/1.21, 1.38, 23.61, 1.28, 1.29, 623/23.51–23.54; 606/151, 280–285, 302, 606/902, 905, 86 R
See application file for complete search history.

(56) References Cited

U.S. PATENT DOCUMENTS 2,436,303 A    2/1948  Jenni et al.
3,409,914 A  * 11/1968  Jones ........................... 623/1.51
(Continued)

FOREIGN PATENT DOCUMENTS

DE    38 08 937 A1    10/1989
EP    1753354 A1    2/2007
(Continued)

OTHER PUBLICATIONS

International Search Report issued in International Application No. PCT/FR2011/050121 dated Apr. 11, 2011 (w/ translation).
(Continued)

*Primary Examiner* — Christopher D Prone
(74) *Attorney, Agent, or Firm* — Oliff PLC

(57) ABSTRACT

A device made up of a textile tubular sheath, which can be implanted in the human body, suitable for containing a filling material and the ends of which are suitable for covering the ends of two portions of a single resected rib. The sheath contains a braid, in which the yarns allow relative movement in relation to one another in order locally to modify the diameter and the shape of the braid, such that the braid not only covers but also encloses the end of one portion of the rib. The sheath is secured to a tip which, allowing the injection of a biocompatible material for filling the sheath, the packing of the braid and the connection by adhesion of the sheath and the braid with the ends of the portions of the rib, is in turn sectional.

17 Claims, 3 Drawing Sheets

(56) References Cited

U.S. PATENT DOCUMENTS

| | | | | |
|---|---|---|---|---|
| 5,980,564 | A | * | 11/1999 | Stinson .................... 623/23.7 |
| 6,312,462 | B1 | * | 11/2001 | McDermott et al. ......... 623/1.25 |
| 8,690,919 | B2 | | 4/2014 | Lange et al. |
| 2004/0019375 | A1 | * | 1/2004 | Casey et al. ................. 623/1.28 |
| 2005/0216011 | A1 | | 9/2005 | Paul |
| 2006/0155296 | A1 | * | 7/2006 | Richter ........................ 606/94 |

FOREIGN PATENT DOCUMENTS

| FR | 2.211.851 | | 7/1974 | |
| FR | 2 353 274 A1 | | 12/1977 | |
| JP | A-4-156840 | | 5/1992 | |
| JP | A 4156840 | * | 5/1992 | ............... A61F 2/02 |
| JP | 2008-500140 A | | 1/2008 | |
| JP | 2009-538207 A | | 11/2009 | |
| RU | 2 145 814 C1 | | 2/2000 | |
| RU | 2 166 292 C1 | | 5/2001 | |

OTHER PUBLICATIONS

International Preliminary Report on Patentability issued in International Application No. PCT/FR2011/050121 dated Aug. 7, 2012 (w/ translation).

* cited by examiner

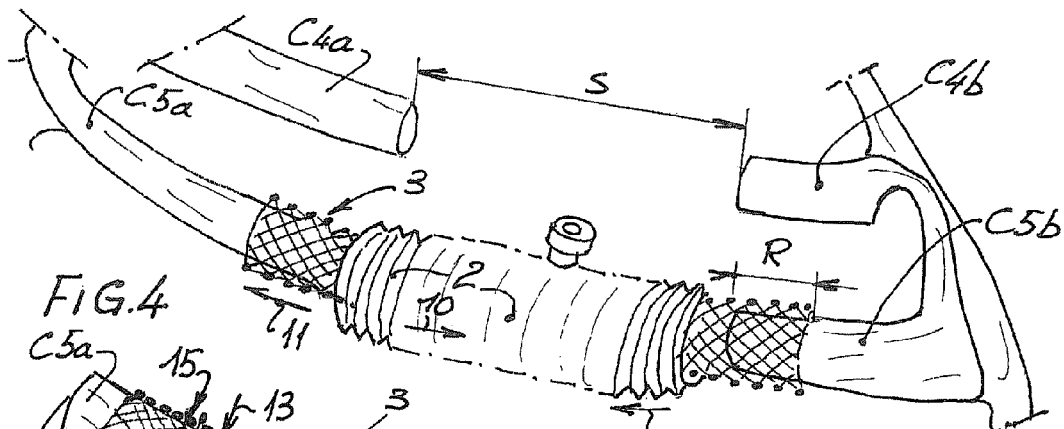
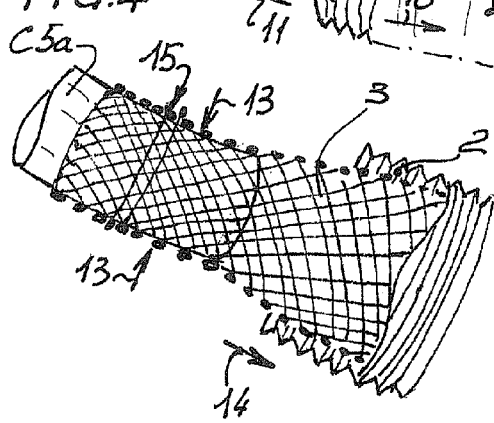
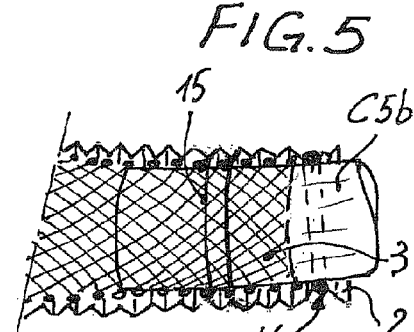
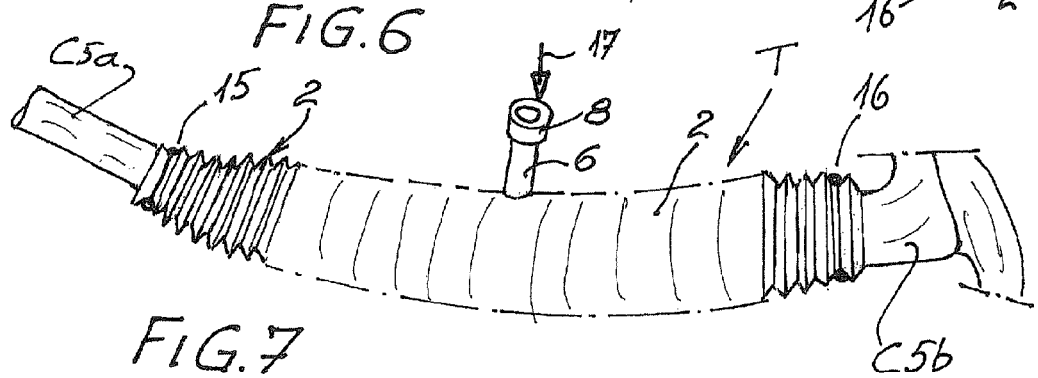
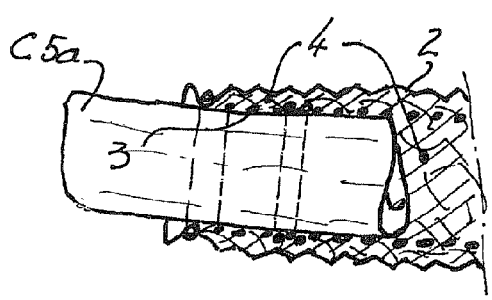

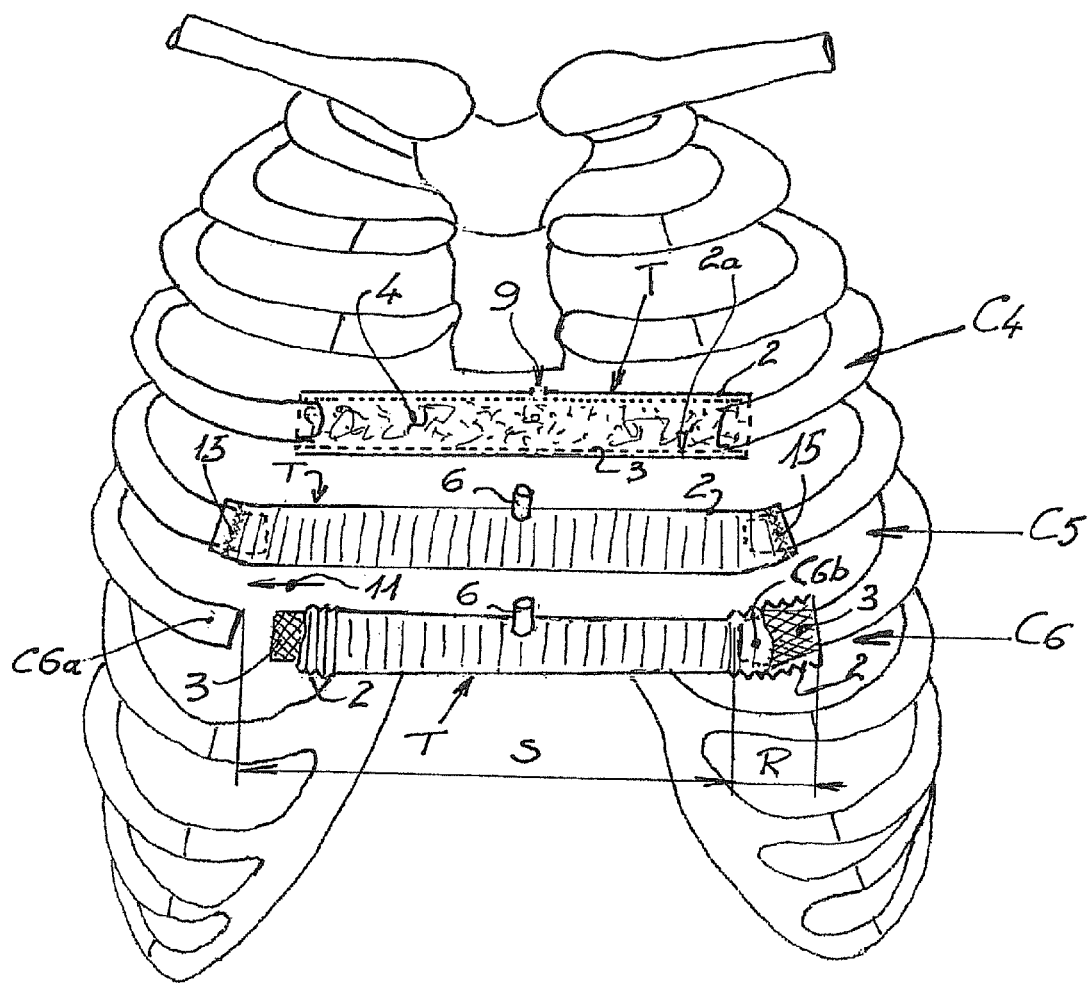

DEVICE FOR OSTEOSYNTHESIS OF THE THORACIC WALL

BACKGROUND OF THE INVENTION

This osteosynthesis device is designed to compensate for the resection of thoracic ribs, after a surgical intervention, in order to avoid the appearance of deformations of the thoracic wall and to stabilize the latter and thus permit better respiratory functions, while at the same time not adversely affecting the esthetic appearance of the chest.

At the present time, thoracic repair, also called reconstruction, is performed using the equipment and implants provided for treating rib fractures following serious trauma, including the splints for supporting bone repairs.

The implants disclosed in the documents RU2145814, RU2166292, DE3808937, U.S. Pat. No. 2,436,303 and US2005/0216011 use rigid transverse bars or splints which are arranged in front of the thoracic wall and which are connected thereto by various fastening means, for example by screws screwed into the bone or by claws stapled to the bone. In their application to the reconstruction of the thoracic cage, these implants are difficult to fit in place, form esthetically unpleasing protrusions on the front of the chest and, in particular, can come loose from the rib, with the risk of migrating and causing perforations to the organs in their proximity.

The implant described in the document US2008/0082101, although more suitable for the reconstruction of the thoracic wall, is composed of a rectilinear splint, on the ends of which claws are fixed by pins or screws, the claws themselves being clamped on the ends of the resected ribs that are to be joined. The rigidity of the splints and of the fixing claws means that they cannot be used in all cases of rib reconstruction and, in order to adapt their size and to shape them, it is necessary to use an ancillary device which, although not complex, affects the final cost of the reconstruction.

Moreover, the fixation of the implants by claws gripped by clamps on the rib injures the latter and has the disadvantage that the stresses transmitted to the implant are concentrated at the grip points, thereby intensifying these injuries and the pain caused to the patient.

The document JP4156840 describes an implant composed of two textile sheets of polyester fibers that are connected by longitudinal seams to each other and around the rib ends delimiting the zone that is to be reconstructed. The tubular sheath thus formed is lined by a mixture of materials bound by a resin. Although each end of the sheath is perfectly adapted by construction to the shape and the dimensions of the rib end on which it is formed, the connection to the rib is insufficient and is unable to transmit to this rib the stresses that it receives. As a result, the implant thus formed is a means for lining the space between the two parts of a resected rib but cannot be considered as a reconstruction tool replacing the resected rib section and transmitting to each part of the rib the forces and stresses experienced by the other part.

The object of the invention is to overcome these disadvantages by making available an osteosynthesis device which is especially adapted to thoracic reconstruction, is easy to use and does not apply localized and damaging stresses to the ribs, both during implantation and when in use, and whose final configuration does not in any way affect the esthetic aspect of the thoracic wall.

BRIEF SUMMARY OF THE INVENTION

As in the prior art set out above, the device according to the invention is composed of a textile tubular sheath, which can be implanted in the human body and is able to contain a filling material, and of which the ends envelop the ends of two parts of one and the same resected rib.

According to the invention, the sheath:
- on the one hand contains a braid, of which the yarns, which are made of metal or polymer, allow relative movements in relation to one another in order to locally modify the diameter and the shape of the braid, such that the latter not only envelops but also tightly holds the end of a rib part,
- and, on the other hand, is integrally connected to a nozzle for injection of a biocompatible material for filling the sheath, lining the braid and adhesively bonding the sheath and the braid to the ends of the rib.

By virtue of this structure, fitting the implant in place firstly involves adapting the length of the unit composed of sheath and braid to the width of the gap between the opposing edges of a rib, added to by the lengths for covering the ends, then rolling back the ends of the sheath on those of the braid in order to disengage these, and engaging each of the ends of the braid on the opposing parts of the rib that is to be reconstructed. The adaptation of the diameter of the braid to the actual diameter of each rib is effected by applying opposite longitudinal forces to the braid in order to increase its diameter or reduce it. Likewise, the shape of the cross section of the braid is adapted to that of the bone, and then the braid is fixed to the bone by manually holding its end surrounding the bone, while pulling it beyond the latter in order to obtain, through the narrowing of the diameter of the braid, its clamping on the bone. If appropriate, the connection of the braid to each rib part is completed by suturing, after which the sheath, hitherto rolled back, is pulled over each of the ends of the braid and beyond these ends, and then fixed to the rib by sutures or staples.

The fitting of the implant is completed by the injection of a filling material into the internal cavity of the sheath. During the hardening of the filling material, the surgeon can shape the implant in order to optimally re-establish the thoracic wall.

It will be appreciated already that, compared to the implants comprising rigid metal components, the fitting of the device according to the invention does not cause any injury to the ribs by scratching and provides reliable and effective fixation, with clamping stresses that are distributed about the entire perimeter of each rib end and do not cause trauma. Moreover, the malleability of the components means that, during the hardening of the filling material, the surgeon is able, without using any tools, to give the implant the shape best suited to the re-establishment of the wall, both in terms of its function and its esthetic appearance.

Finally, the injected material not only ensures that the sheath is filled, but also that it is connected to the parts of the rib and to the braid, which reinforces it in the manner of a truss.

Once the injected material has hardened and no longer risks flowing out of the sheath, the nozzle is cut and withdrawn.

In one embodiment of the invention, the textile tubular sheath has a porosity allowing air to escape during the pouring-in of the filling material, but opposing the escape of this material.

This permits homogeneous filling, without gas pockets.

Advantageously, the braid, the tubular sheath and the injection nozzle are made of materials and with dimensions allowing them to be cut using scissors.

This arrangement, which reduces the instrumentation to a single pair of scissors and removes the need for cutting pliers, simplifies the adjustment of the length of the components of the tubular body, improves the level of precision and reduces the fitting time.

BRIEF DESCRIPTION OF THE DRAWINGS

Other features and advantages will become clear from the following description and by reference to the attached schematic drawing, in which:

FIGS. 3 to 7 are partial views in elevation and partial cross section of the implant in different phases of the reconstruction of a lateral rib;

FIG. 8 is a front view, in partial cross section, of a thoracic cage having undergone resection of the sternum and of three ribs, when it is in the process of frontal reconstruction, and showing, from the bottom upward, at C6 the placement of the implant, at C5 the implant after it has been filled, and at C4 the implant when completed and in section.

DETAILED DESCRIPTION OF THE INVENTION

Figure 1:
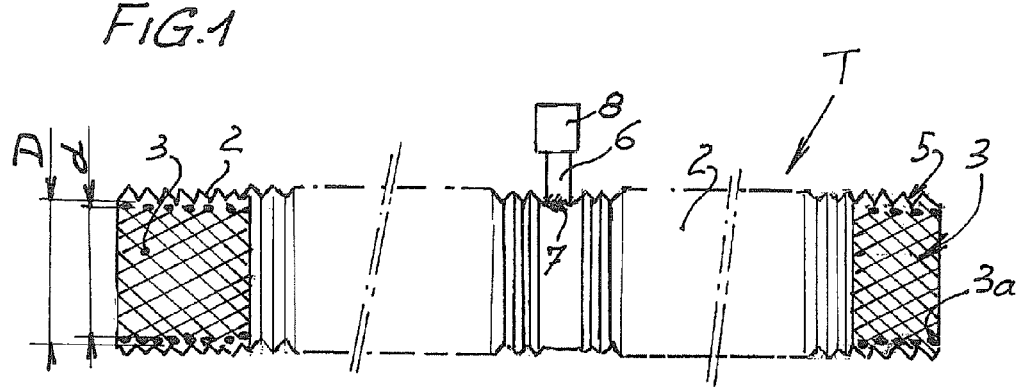
FIG. 1 is a view in side elevation of an embodiment of the body of the implant with partial sectioning of its ends.

As is shown in FIG. 1, the device according to the invention is formed by a tubular body T, itself composed of an outer textile sheath 2 and an inner braid 3.

The textile sheath 2 is obtained by the weaving or knitting of yarns of biocompatible material that can be implanted in the human body, for example polyesters, polytetrafluoroethylene, polyethylene, propylene, etc.

The texture of the weave or the structure of the knit is defined such that the sheath 2 is porous to air and gases, but not to the filling material 4, which is defined further below.

The internal diameter $\underline{D}$ of the sheath 2 is between 8 and 14 millimeters, which values correspond to the most common dimensions of a human rib. Said internal diameter can be smaller for use in animals.

Preferably, the wall of the sheath 2 is crimped or corrugated with deformable corrugations 5, facilitating the adjustment of its configuration and its length when being placed in position. These corrugations have a triangular cross section in the figures, but they can have any other cross section, for example in the shape of an arc of a circle or trapezoid.

According to one feature of the invention, the sheath 2 is equipped with an injection nozzle 6 which is formed by a textile or nontextile tubular body made of biocompatible material. One of the ends of this nozzle is joined to the sheath 2, by a weld or seam 7, while its free end may or may not be provided with attachment means 8, permitting its attachment to a dispenser of filling material, for example to the nozzle of a syringe.

The nozzle 6 has a length of between 3 and 10 millimeters, is arranged to protrude outward, radially or not, and communicates with the interior of the sheath 2 via a hole 9, represented at C and at the top of FIG. 8.

The braid 3 is composed of yarns 3a of biocompatible material that can be implanted in the human body, for example of a metal or a synthetic or polymeric material. A nonmagnetic yarn is preferred in order to avoid interfering with the results of medical imaging procedures, for example by nuclear magnetic resonance, performed postoperatively.

In one embodiment, the braid is composed of metal yarns braided with an angulation of between 30 and 60 degrees and with the possibility of moving relative to one another so as to vary the nominal diameter of the braid, upward or downward, within a range of values. The diameter of the yarns is between 0.1 and 0.3 millimeter, and the braid is formed by interlacing of 16 to 48 strands, depending on the nominal diameter.

The constituent material of the yarns is, for example, a stainless steel, such as the one designated by 316LVM. It can also be composed of a superalloy, for example a cobalt-chromium-nickel-molybdenum-iron alloy specified in standards ASTM F 1058 and ISO 5832-7, or an alloy of nickel and titanium known under the name Nitinol.

The external diameter $\underline{d}$ of the braid 3 at rest is equal, except for functional play, to the internal diameter of the sheath 2 at rest, such that each of them can be moved longitudinally in relation to the other.

In practice, the tubular implant T, formed by the sheath 2 containing a braid 3, is chosen from a series of implants that differ in terms of their internal diameter of between 8 and 14 millimeters, with increments of 1.5 to 2 millimeters. Each of the elements of the series has a length of the order of 30 centimeters, possibly as much as 50 centimeters in some applications, and is made of materials and of yarns that can be cut using scissors.

Figure 2:
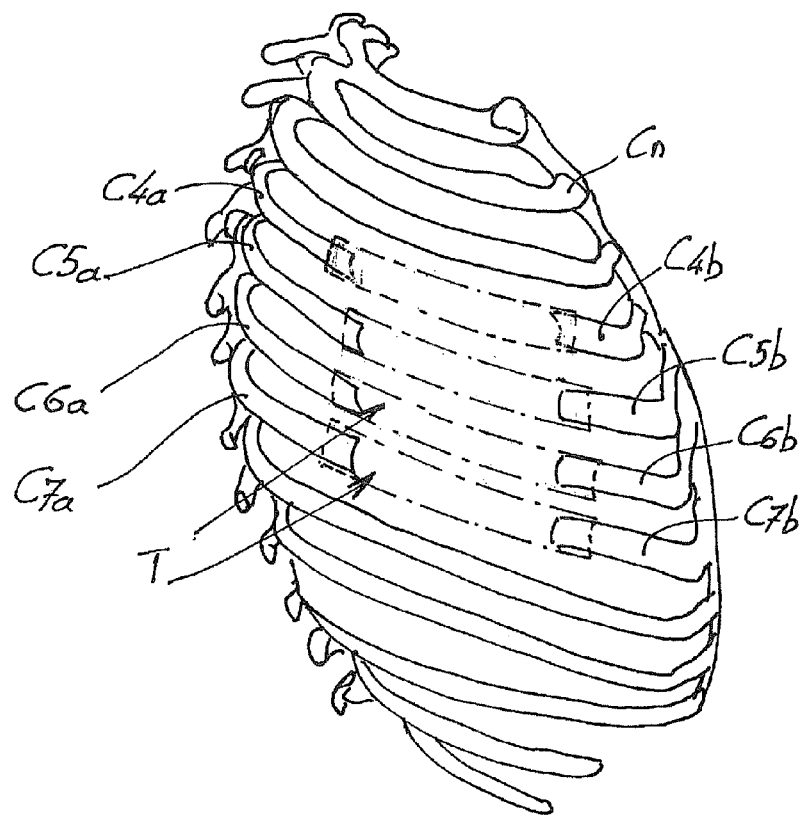
FIG. 2 is a view in side elevation of a human thoracic cage showing some of the lateral zones that can be reconstructed.

To construct an intercostal connection between the two parts Cna and Cnb of an nth rib Cn that has been resected, as is shown in FIGS. 2 and 3 for the rib C5 separated into C5a and C5b, the surgeon measures the distance $\underline{S}$ between the two parts C5a and C5b and determines the length that the tubular implant $\underline{T}$ must have in order to provide a covering $\underline{R}$ of the rib parts by a distance of between 5 and 15 millimeters. Having chosen an implant with a diameter corresponding to the dimensions and cross sections of the rib parts, the surgeon cuts the implant to the necessary length.

Then, as is shown by the arrow 10 in FIG. 3, the surgeon rolls back the sheath 2 on each of the ends of the braid 3, in order to facilitate the engagement thereof on each of the rib parts in the direction of the arrows 11. During this movement, the diameter and the shape of the cross section of the braid 3 are adapted manually to those of the rib part C5a or C5b.

At the end of the engagement movement, and while the braid 3 is pinched manually in the direction of the arrows 13 on the rib part, for example C5a in FIG. 4, its body arranged outside the rib is drawn in the direction of the arrow 14 in order to bring about a reduction in the diameter of its end on the rib part and to ensure its anchoring thereon.

Although the radial clamping of the ends of the braid 3 on the parts C5a and C5b of the rib suffices to ensure the positioning of the braid, it may sometimes be necessary to lock the latter in place by means of a suture thread 15, visible in FIG. 4.

In the subsequent phase, and as is shown in FIG. 5, the two ends of the sheath 2, hitherto rolled back on the braid, are returned to position above these ends, and even beyond them, and are then fixed on the bone by a suture thread 16 or by stapling.

It is then possible to proceed with the rest of the intercostal reconstruction which, as is shown by the arrow 17 in FIG. 6, involves connecting the nozzle 6 to a source of filling material 4, for example to a connector formed at the end of a syringe. During the injection, the material enters the internal cavity 2a of the sheath 2 and, by virtue of the porosity of this sheath, drives out the air and gases contained in this cavity.

FIG. 7 shows that the material 4 filling the cavity 2a positions itself between the sheath 2 and the rib part C5a, traverses the braid 3 and, in the end zones of this braid, forms a complementary agent binding the implant with the parts C5a and C5b of the rib.

While the filling material hardens or polymerizes, the surgeon can manually shape the implant such that it assumes the shape best adapted to the needs of the reconstruction, the respiratory functions and the desired esthetic aspect.

The filling material is of a type already used in reconstructive surgery, for example for the fixation of prosthesis shafts, and composed of methylmethacrylate cement.

In one embodiment, this cement is a calcium phosphate cement obtained by mixing two phases:
  a powder phase composed of a mixture of tetracalcium phosphate, tricalcium phosphate and calcium glycerophosphate,
  and a liquid phase containing calcium hydroxide, phosphoric acid and water.

For the low-density version to be injected by syringe, the solid phase of the mixture contains polydimethylsiloxane.

When implantation is completed, the injection nozzle 6 is cut flush with the sheath 2, as is shown at C4 in FIG. 8, without the need to close it, since it is already closed by the material 4.

In the implant thus obtained, the material 4 is stiffened by the braid 3, which then behaves as a truss, such that the device has a strength at least as great as that obtained using implants with metal clips, and it anchors to the ribs with peripheral forces, i.e. forces not localized at a few points, and less damaging to the bone.

This mode of reconstruction of the thoracic cage can be applied to the ribs from the first to the tenth and can be used for lateral repair, as shown schematically in FIG. 2, and also for frontal repair, as shown schematically in FIG. 8.

Furthermore, in FIG. 8, the reference signs for the components of the implant and for the phases of placement thereof are the same reference signs as those used for the description with reference to FIGS. 1 to 7.

The invention claimed is:

1. A device for osteosynthesis of the thoracic wall, comprising:
   a textile tubular sheath which can be implanted in the human body and is able to contain a filling material, the textile tubular sheath having deformable corrugations at a first end and at a second end that are integrally formed with one or more portions without corrugations between the first and second ends, such that the deformable corrugations form a single, unitary body with the one or more portions without corrugations between the first and second ends, the first and second ends being able to envelop, respectively, a first end and a second end of a resected rib,
   a braid having a first end and a second end, the braid being disposed inside of the sheath and being constructed of biocompatible yarns, which are made of metal or polymer, the biocompatible yarns being configured to allow relative movements in relation to one another in order to locally modify an external diameter and a shape of the braid, such that each end of the braid not only is able to envelop but also is able to tightly hold each end of the resected rib, respectively, wherein the braid has, before implantation, an external diameter equal to an internal diameter that the sheath has before implantation, and wherein the deformable corrugations of the sheath are movable in a first direction to cover the entire braid when the braid envelops the first end and the second end of the resected rib to thereby secure the braid to the resected rib, and wherein the sheath is movable in a second direction, which is opposite of the first direction, to uncover the braid so that the braid is able to engage the first end and the second end of the resected rib; and
   a nozzle for injection of a biocompatible material, wherein the nozzle is both (i) integrally connected to the textile tubular sheath and (ii) removable from the textile tubular sheath, penetrating the braid and adhesively bonding the first and second ends of the sheath and of the braid to the first and second ends of the resected rib, respectively.

2. The device for osteosynthesis of the thoracic wall as claimed in claim 1, wherein the textile tubular sheath has a porosity allowing air and gases to escape during the injection of the biocompatible material but opposing the escape of the biocompatible material.

3. The device for osteosynthesis of the thoracic wall as claimed in claim 1, wherein the injection nozzle is formed by a tubular body which protrudes outside the textile sheath and of which one end is connected to the sheath by a weld or seam, while the other end is provided with an attachment piece for attachment to means for injecting the biocompatible material.

4. The device for osteosynthesis of the thoracic wall as claimed in claim 1, wherein the braid, the tubular sheath and the injection nozzle are made of materials and with dimensions allowing them to be cut using scissors.

5. The device for osteosynthesis of the thoracic wall as claimed in claim 1, wherein:
   the braid is formed by biocompatible yarns having an external diameter of between 0.1 and 0.3 millimeter, and
   the tubular sheath is formed by the weaving or knitting of yarns of biocompatible material selected from the group consisting of polyesters, polytetrafluoroethylene, polyethylene and polypropylene.

6. The device for osteosynthesis of the thoracic wall as claimed in claim 1, wherein the sheath and the braid constitute a tubular implant portion of the device and the tubular implant portion has an internal diameter ranging from 8 to 14 millimeters in increments of 1.5 to 2 millimeters.

7. The device for osteosynthesis of the thoracic wall as claimed in claim 2, wherein:
   the braid is formed by biocompatible yarns having an external diameter of between 0.1 and 0.3 millimeter, and
   the tubular sheath is formed by the weaving or knitting of yarns of biocompatible material selected from the group consisting of polyesters, polytetrafluoroethylene, polyethylene and polypropylene.

8. The device for osteosynthesis of the thoracic wall as claimed in claim 1, wherein:
   the braid is formed by biocompatible yarns having an external diameter of between 0.1 and 0.3 millimeter, and
   the tubular sheath is formed by the weaving or knitting of yarns of biocompatible material selected from the group consisting of polyesters, polytetrafluoroethylene, polyethylene and polypropylene.

9. The device for osteosynthesis of the thoracic wall as claimed in claim 3, wherein:
   the braid is formed by biocompatible yarns having an external diameter of between 0.1 and 0.3 millimeter, and
   the tubular sheath is formed by the weaving or knitting of yarns of biocompatible material selected from the group consisting of polyesters, polytetrafluoroethylene, polyethylene and polypropylene.

10. The device for osteosynthesis of the thoracic wall as claimed in claim 4, wherein:
    the braid is formed by biocompatible yarns having an external diameter of between 0.1 and 0.3 millimeter, and
    the tubular sheath is formed by the weaving or knitting of yarns of biocompatible material selected from the group consisting of polyesters, polytetrafluoroethylene, polyethylene and polypropylene.

11. The device for osteosynthesis of the thoracic wall as claimed in claim 1, wherein the first and second ends of the textile tubular sheath are configured to be fixed to the first and second ends of the resected rib, respectively, by suture thread.

12. The device for osteosynthesis of the thoracic wall as claimed in claim 1, wherein
the first and second ends of the textile tubular sheath are configured to be fixed to the first and second ends of the resected rib, respectively, by a staple.

13. The device for osteosynthesis of the thoracic wall as claimed in claim 1, wherein
the first and second ends of the braid are configured to be fixed to the first and second ends of the resected rib, respectively, by suture thread.

14. The device for osteosynthesis of the thoracic wall as claimed in claim 1, wherein the tubular sheath has one or more corrugated portions between the first and second ends surrounded by portions without corrugations.

15. A device for osteosynthesis of the thoracic wall, comprising:
a textile tubular sheath which can be implanted in the human body and is able to contain a filling material, the textile tubular sheath having deformable corrugations at a first end and at a second end that are integrally formed with one or more portions without corrugations between the first and second ends, such that the deformable corrugations form a single, unitary body with the one or more portions without corrugations between the first and second ends, each of the first and second ends are able to envelop, respectively, a first end and a second end of a resected rib;
a braid having a first end and a second end, the braid being disposed inside of the sheath and being constructed of biocompatible yarns, which are made of metal or polymer, the biocompatible yarns being configured to allow relative movements in relation to one another in order to locally modify an external diameter and a shape of the braid, such that each end of the braid not only is able to envelop but also is able to tightly hold each end of the resected rib, respectively, wherein the braid has, before implantation, an external diameter equal to an internal diameter that the sheath has before implantation, and
wherein the deformable corrugations of the sheath are movable in a first direction to cover an entire outer surface of the braid when the braid envelops the first end and the second end of the resected rib to thereby secure the braid to the resected rib, and wherein the sheath is movable in a second direction, which is opposite of the first direction, to uncover the braid so that the braid is able to engage the first end and the second end of the resected rib; and
a nozzle disposed at a center portion of the tubular sheath without corrugations and being perpendicular to an axial direction of the textile tubular sheath for injection of a biocompatible material and being integrally connected to the textile tubular sheath, wherein the nozzle is both (i) integrally connected to the textile tubular sheath and (ii) removable from the textile tubular sheath, wherein deformable corrugations are adjacent to and integrally formed with each of a first end and a second end of the center portion of the tubular sheath without corrugations, the biocompatible material for filling the sheath, penetrating the braid and adhesively bonding the first and second ends of the sheath and of the braid to the first and second ends of the resected rib, respectively.

16. The device for osteosynthesis of the thoracic wall as claimed in claim 15, wherein the nozzle is equidistant between the first end and the second end of the textile tubular sheath.

17. A device for osteosynthesis of the thoracic wall, comprising:
a textile tubular sheath which can be implanted in the human body and is able to contain a filling material, the textile tubular sheath having deformable corrugations at a first end and at a second end that are integrally formed with one or more portions without corrugations between the first and second ends, such that the deformable corrugations form a single, unitary body with the one or more portions without corrugations between the first and second ends, wherein each of the first and second ends are able to envelop, respectively, a first end and a second end of a resected rib, wherein the braid has, before implantation, an external diameter equal to an internal diameter that the sheath has before implantation, and
wherein the deformable corrugations of sheath are movable in a first direction to cover an entire outer surface of the braid when the braid envelops the first end and the second end of the resected rib to thereby secure the braid to the resected rib, and wherein the sheath is movable in a second direction, which is opposite of the first direction, to uncover the braid so that the braid is able to engage the first end and the second end of the resected rib;
a braid having a first end and a second end, the braid being disposed inside of the sheath and being constructed of biocompatible yarns, which are made of metal or polymer, the biocompatible yarns being configured to allow relative movements in relation to one another in order to locally modify the diameter and the shape of the braid, such that each end of the braid not only is able to envelop but also is able to tightly hold each end of the resected rib, respectively; and
a nozzle for injection of a biocompatible material, wherein the nozzle is (i) integrally connected to the textile tubular sheath and (ii) removable from the textile tubular sheath, the biocompatible material for filling the sheath, penetrating the braid and adhesively bonding the first and second ends of the sheath and of the braid to the first and second ends of the resected rib, respectively,
wherein the tubular sheath is configured to have a variable length such that the tubular sheath is able to be retracted to expose the braid and expanded to cover the ends of the braid.

* * * * *